United States Patent [19]
Butler

[11] Patent Number: 5,122,909
[45] Date of Patent: Jun. 16, 1992

[54] MICROLENS CONNECTOR

[76] Inventor: Robert B. Butler, 650 Union Valley Rd., R.D. 8, Mahopac, N.Y. 10541

[21] Appl. No.: 720,717

[22] Filed: Jun. 25, 1991

[51] Int. Cl.⁵ .............................................. G02B 7/02
[52] U.S. Cl. ................................... 359/809; 359/818; 359/820; 359/830
[58] Field of Search ............... 359/802, 803, 805, 808, 359/809, 810, 811, 812, 815, 818, 819, 820, 822, 823, 825, 828, 829, 830; 385/39, 33

[56] References Cited
U.S. PATENT DOCUMENTS 2,808,762 10/1957 De Grave, Jr. ..................... 359/830
4,762,395 8/1988 Gordon et al. ..................... 359/820

Primary Examiner—Loha Ben

[57] ABSTRACT

An optical magnifying lens installed in the hub of a plier-grip or similar instrument and which also holds the instruments's mating halves together in a snugly rotatable position.

4 Claims, 2 Drawing Sheets

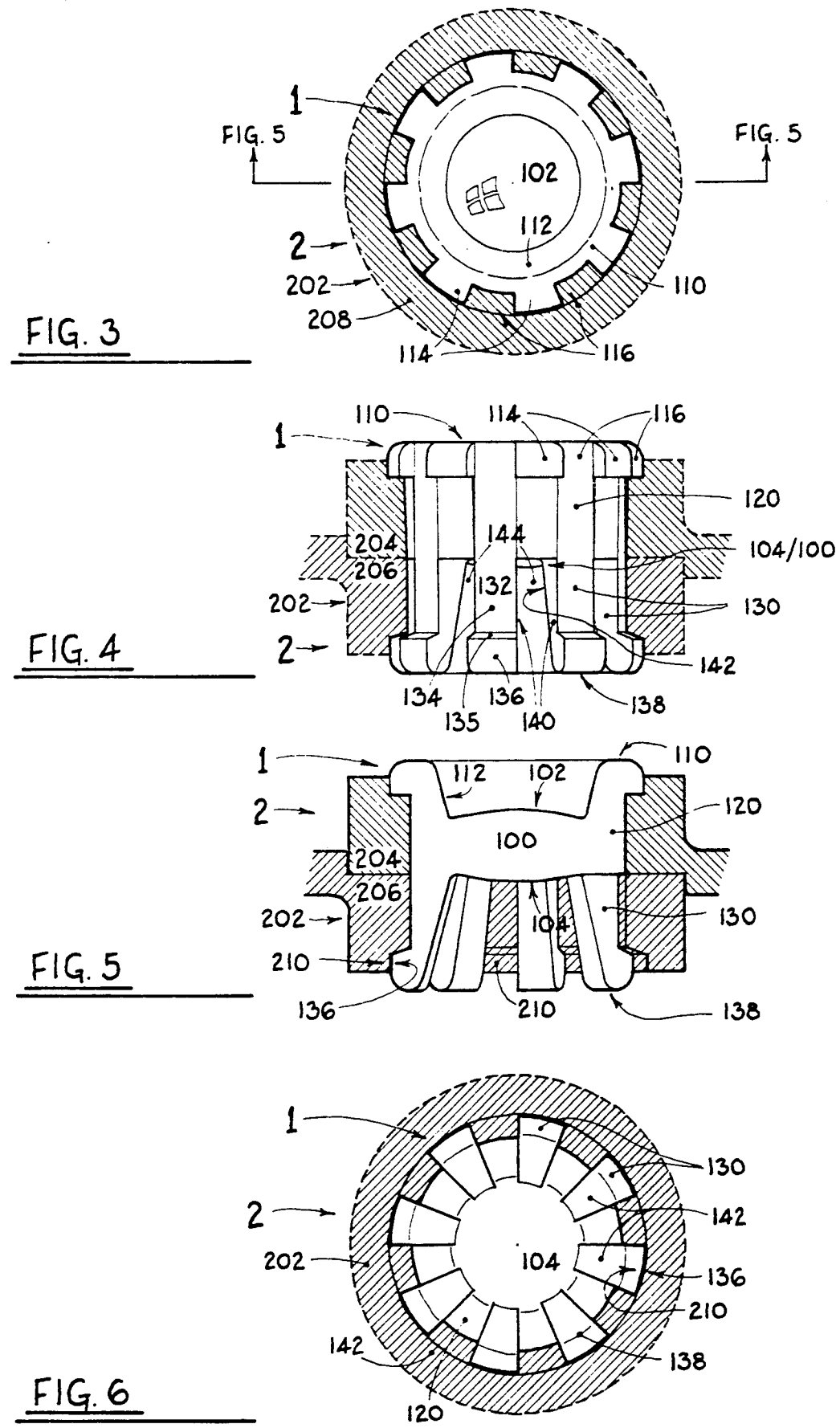

MICROLENS CONNECTOR

FIELD OF THE INVENTION

The invention relates to the need in certain kinds of industrial, medical, or consumer-oriented work for a powerful magnifier combined with a hand-held instrument to produce a tool in which two functions exist in one implement for purposes of efficiency or novelty.

BACKGROUND OF THE INVENTION

In certain industrial, medical, and/or consumer activities, the operator of a hand-held tool occasionally needs a powerful magnifier to examine part of the work being performed without having to lay aside the instrument being held. An example of such a situation is the removal of a tick from a person or animal: this requires the use of a hand-held gripping means by which the imbedded parasite is retracted from the skin of the host, then the tick's mouthparts need to be examined immediately afterward by a powerful magnifier to determine whether or not they were broken during removal, and this knowledge determines what the remover will do next. Here a powerful magnifier built into the hand-held gripping means would be advantageous, as the remover while retracting the tick may be trying to calm the anxious host, may be working unassisted, and/or may be several feet or even several miles away from access to a variety of tools. In many other fields of work or recreation, the availability of such a multiple-use tool would offer the user a similar advantage.

SUMMARY OF THE INVENTION

Accordingly, the principal object of the disclosed invention is to provide a user of certain hand-held instruments the advantage of having a powerful magnifier without reaching for a second instrument. In one embodiment of the invention, the magnifier is fitted into the interconnecting region of the two mating halves of a plier-grip instrument, so the parent tool may be used to grip and manipulate small objects and then examine such work at any time through the microlens mounted in the instrument's hub without laying the parent tool aside or even letting go of its handles.

A principle feature of the invention is that the incorporated microlens has great power of magnification. For example, in the original embodiment for which the invention was designed (a plier-grip instrument for removing ticks from people and animals), the hub-mounted lens has 20 power magnification, but the invention's range of optic magnification could be as high as 60 or 80 power.

Another feature of the invention is that the relatively thin microlens is located centrally between the top and bottom of the thicker hub of the parent instrument, so that the two lens surfaces have a deep recess which protects them from damage by scratching.

Another feature of the invention is that the rims around the microlens' two recessed surfaces are bevelled outward to facilitate lens viewing and cleaning of lens surfaces.

Another feature of the invention is that it can be manufactured inexpensively from high-grade clear plastic. This material has great strength, is more transparent than window glass, is not brittle like glass, can be manufactured to small tolerances that minimize optical distortion or haze, and can be molded into intricate shapes. Moreover, the invention's design allows it to be manufactured economically by a plastic injection mold that requires no cams, undercuts, or extensive arrays of sprues or knockout pins. However, part or all of the invention may be manufactured from materials other than plastic or methods other than injection molding process.

An outstanding feature of the invention is that it also acts as the connector for the mating halves of the parent instrument. The underside of the lens is ringed by a plurality of hooked prongs or similar connecting means, which when inserted into the hub of the instrument seat into the hub's underside to create a method of holding together the mating halves that requires no washers, nuts, or cotter pins, and that said connection maintains a snugly rotatable operation of the mating halves for the life of the tool.

Another feature of the invention is that it is located in the hub of the parent instrument so the seam plane of the instrument's surrounding mating halves lies between the thickness of the lens, allowing the mass of the lens to absorb much of the unit shear stresses incurred in the instrument's hub during its use.

In consideration of the prior art:

As for any prior art that might negate the patentability of the disclosed invention, the inventor conducted an exhaustive search of all patents of several classes/sub classes related to lenses and lense supports, a total of 605 patents in all. Of these, none was similar to the disclosed invention. However, to clarify the obvious differences between the disclosed invention and the general nature of any prior art, the prior art most nearly assimilating the disclosed invention is described below:

Heun, in U.S. Pat. No. 4,863,241, describes a printer's loupe that is [from the abstract] "for use in the repair of a printing plate mounted on a printing cylinder, the loupe comprising a body having integral means for supporting said loupe on the surface of said cylinder . . . means, attached to said body, for illuminating said printing plate . . . means, attached to said body, for supplying power to said illuminating means . . . and . . . means, mounted to said body, for magnifying a portion of said printing plate." First, Heun's patent is for a *magnifier only*: no part of it serves any function other than to assist in its magnifying capabilities; whereas the disclosed invention is a *combined* lens *and* connector: its properties of magnification are not designed to be utilized without mechanical incorporation into a parent instrument. Second, examination of the drawings alone of Heun's patent indicates that its function requires no incorporation into, or even touching of, any instrument or machinery it may be used with. In conclusion, each of these elements alone teaches away from the essential nature of the disclosed invention, and thus for each of these reasons exclusive of the others the disclosed invention is patentable over Heun.

BRIEF DESCRIPTION OF THE DRAWINGS

These and other aspects, features, and advantages of the disclosed invention may be better understood by a detailed description of the preferred embodiment of the invention as revealed by the following drawings, in which:

FIG. 3 is a top view of the above embodiment of the invention, showing the recessed upper lens surface surrounded by the bevelled upper rim.

FIG. 4 is a side view of the above embodiment of the invention, showing the upper connecting means (or rim), cylindrical shell, and lower connecting means that ring the microlens.

FIG. 5 is a section through the above embodiment's longitudinal axis, showing the upper connecting means, cylindrical shell, and lower connecting means that ring the microlens, and how the upper and lower connecting means hold together the mating halves of the parent instrument.

FIG. 6 is a bottom view of the above embodiment of the invention, showing the recessed lens surface surrounded by the lower connecting means.

DESCRIPTION OF THE PREFERRED EMBODIMENT OF THE INVENTION

Figure 1:
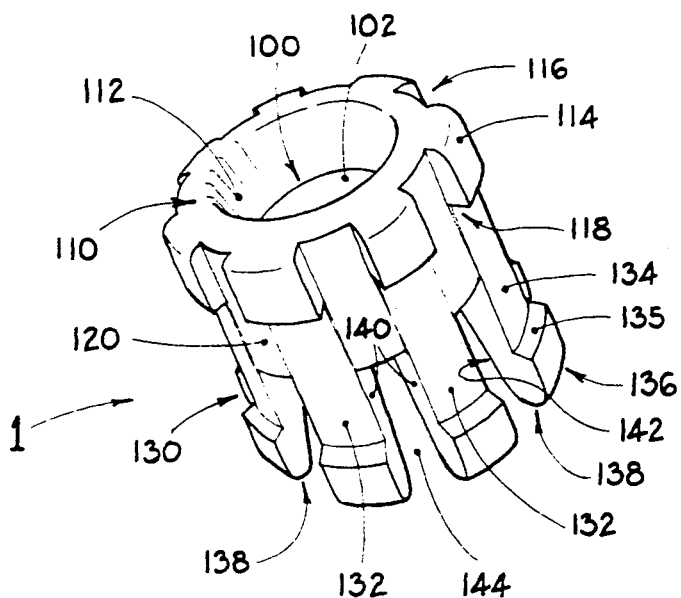
FIG. 1 is a perspective view of a particular embodiment of the invention as it exists prior to its incorporation into the hub of a parent instrument.

Referring to FIG. 1 of the drawings, this perspective view shows the microlens connector 1 with its recessed lens 100, upper connecting means (which in this particular embodiment consists of a continous rim) 110, cylindrical shell 120, and lower connecting means (which in this particular embodiment consists of a plurality of prongs) 130. Lens 100 has an upper convex surface 102 and lower convex surface 104 (not visible in this view). Rim 110 has a bevelled inner face 112, plurality of overhanging knurls 114 around its outside, and a slot 116 between each pair of knurls 114. The cylindrical shell 120 has knurls 114 around rim 110 at its top and plurality of prongs 130 projecting from its underside. Each prong 130 has a shaft 132 and hook 136; and a gap 144 exists between each pair of prongs 130. Each prong shaft 132 has sides 140, bevelled inner face 142, and outer face 134 which projects outward at bevel 135 to form below it hook 136. Hook 136 fits into inlet 210 (not visible) of the parent instrument 2 (not shown) and has an intermittent lower rim 138.

Figure 2:
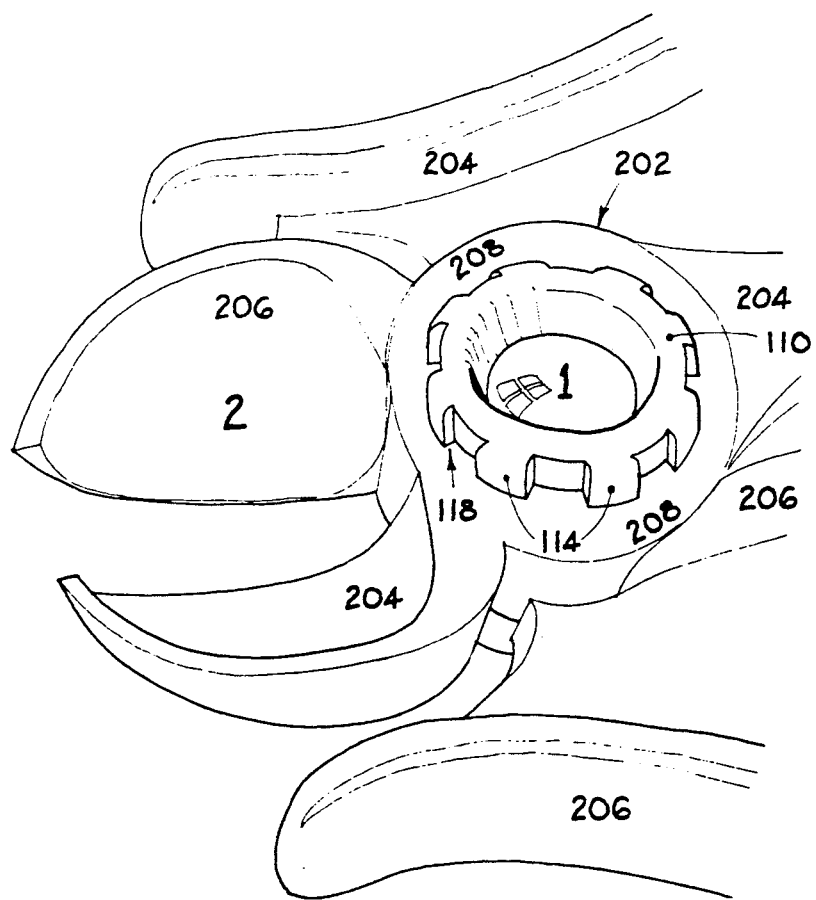
FIG. 2 is a perspective view of the above embodiment of the invention after its incorporation into the hub of a parent instrument.

Referring to FIG. 2, this perspective view shows the microlens connector 1 incorporated into the hub 202 of instrument 2, which consists of mating halves 204 and 206 that intersect at hub 202 where they are held together by microlens connector 1. Rim 110 protrudes above the upper surface 208 of hub 202, and the undersides of knurls 114 protruding from rim 100 rest against surface 208.

Referring to FIG. 3, this top view of the microlens connector 1 as incorporated into instrument 2 (shaded portion) shows the lens' recessed upper surface 102 encircled by the bevelled inner face 112 of rim 110. On the outside of rim 110 are overhanging knurls 114 with slots 116 between each pair of knurls 114, and the knurls' undersides on upper surface 208 of hub 202.

Referring to FIG. 4, this side view of the microlens connector 1 shows rim 110, overhanging knurls 114 with slots 116 between each pair of knurls 114, cylindrical shell 120, and prongs 130. Each prong shaft 132 has an outer face 134 with bevel 135, sides 140, gaps 144 in between sides 140, and bevelled inner face 142; and each prong hook 136 has a lower rim 138. Just under cylindrical shell 120 is the lower surface 104 of lens 100. The shaded area around piece 1 is hub 202 of instrument 2, consisting of mating halves 204 and 206.

Referring to FIG. 5, this section through the longitudinal axis of microlens connector 1 shows the lens 100 and its recessed convex surfaces 102 and 104, as well as bevelled inner face 112, rim 110, cylindrical shell 129, prongs 130, lower rim 138, and prong hooks 136 fitting into the instrument's bevelled inset 210. The shaded area around piece 1 is hub 202 of instrument 2, consisting of mating halves 204 and 206.

Referring to FIG. 6, this bottom view of microlens connector 1 as incorporated in instrument 2 (shaded portion) shows the lens' recessed lower surface 104 encircled by bevelled inner faces 142 of prongs 130, whose hooks 136 fit into inset 210 of instrument 2, and whose bottommost surfaces form form lower rim 138. In each prong gap 142 appears the underside of cylindrical shell 120.

OPERATION OF THE PREFERRED EMBODIMENT OF THE INVENTION

Microlens connector 1 is incorporated into instrument 2 by aligning the mating halves 204 and 206 of instrument 2, then inserting the prong end of piece 1 longitudinally into a central cylindrical cavity of hub 202. As prong hooks 136 contact the hub cavity's upper inner edge, the resilient prongs 130 bend inward and remain in this position as piece 1 slides through said cavity of hub 202. As prong bevels 135 pass inset 210 of instrument 2, prongs 130 spring back to create a clamping action between them and the overhanging knurls 114 at rim 110 which holds together the mating halves 204 and 206 of instrument 2. After incorporation of microlens connector 1, instrument 2 may be used for its intended purpose, with piece 1 always holding mating halves 204 and 206 together in a snugly rotatable manner; and at any time during such use, the operator may look through lens 100 to examine at great magnification an object held underneath without laying aside instrument 2.

As is apparent from the foregoing specification, the disclosed invention provides a simple method of performing and examining certain kinds of work with only one hand instrument, and in a way that allows for the more economical manufacture of said instrument.

Although the invention has been described in a preferred form with a certain degree of particularity, it is understood that the present disclosure of this particular embodiment has been made only by way of example, and that numerous changes in construction details and the combination and arrangement of its various parts be resorted to without departing from the spirit and scope of the invention as hereinafter claimed; and it is intended that the patent shall cover, by suitable expression in the appended claims, whatever features of patentable novelty that exist in the invention disclosed.

What is claimed is:

1. A means of optical magnification located at an intersection of two mating halves of a plier-grip or similar kind of instrument, and which simultaneously serves as the connecting means for the instrument's two mating halves, comprising:
   a. a centrally located magnifying lens having two surfaces and made of a transparent material;
   b. an overhanging means extending outward from around one of the lens surfaces;
   c. an overhanging means extending outward from around the other of the lens surfaces, which combines with the overhanging means around said one of the lens surfaces to create a longitudinal clamping action that holds together in a snugly rotatable position the mating halves of a plier-grip or similar kind of instrument in which the invention is installed.

2. A device as described in claim 1, wherein the lens is located so the intersecting plane of surrounding mating halves of a parent instrument passes between the two surfaces of the lens.

3. A device as described in claim 1, wherein the material around the two lens surfaces forms a raised rim around each lens surface.

4. A device as described in claim 2, wherein the inner faces of the rims around the two lens surfaces bevel outward from each lens surface.

* * * * *